United States Patent
Chien et al.

(10) Patent No.: US 7,767,719 B2
(45) Date of Patent: Aug. 3, 2010

(54) ANTHRACENEDIONE COMPOUNDS

(75) Inventors: Du-Shieng Chien, Guilford, CT (US);
Yi-Wen Chu, His-Chih (TW);
Wu-Chang Chuang, Yonghe (TW);
Ming-Chung Lee, Tucheng (TW)

(73) Assignee: SunTen Phytotech Co., Ltd., Jhonghe (TW)

( * ) Notice: Subject to any disclaimer, the term of this patent is extended or adjusted under 35 U.S.C. 154(b) by 63 days.

(21) Appl. No.: 11/733,041

(22) Filed: Apr. 9, 2007

(65) Prior Publication Data

US 2007/0238784 A1    Oct. 11, 2007

Related U.S. Application Data

(60) Provisional application No. 60/790,340, filed on Apr. 7, 2006.

(51) Int. Cl.
*A01N 37/00* (2006.01)
*A01N 35/00* (2006.01)
*A61K 31/21* (2006.01)
*A61K 31/12* (2006.01)

(52) U.S. Cl. .................. 514/680; 514/679; 514/685; 544/100; 544/156

(58) Field of Classification Search .................. 514/510, 514/680, 685; 544/100, 156
See application file for complete search history.

(56) References Cited

U.S. PATENT DOCUMENTS

| | | | |
|---|---|---|---|
| 3,881,000 | A | 4/1975 | Freidmann et al. |
| 4,966,918 | A | 10/1990 | Watanabe et al. |
| 5,053,431 | A | 10/1991 | Watanabe et al. |
| 5,316,768 | A | 5/1994 | Hughes et al. |
| 5,476,952 | A | 12/1995 | Su et al. |
| 5,648,258 | A | 7/1997 | Odom |
| 6,187,313 | B1 | 2/2001 | Segelman |
| 6,800,615 | B2 | 10/2004 | Cichewicz et al. |
| 6,875,746 | B1 | 4/2005 | Nair et al. |
| 6,903,076 | B2 | 6/2005 | Cichewicz et al. |
| 7,132,403 | B2 | 11/2006 | Cichewicz et al. |
| 2001/0047032 | A1 | 11/2001 | Castillo et al. |
| 2002/0164387 | A1 | 11/2002 | Wei et al. |
| 2003/0229032 | A1 | 12/2003 | Cichewicz et al. |
| 2004/0106686 | A1 | 6/2004 | Cichewicz et al. |
| 2004/0116361 | A1 | 6/2004 | Cichewicz et al. |
| 2004/0121968 | A1 | 6/2004 | Ljubimov et al. |
| 2004/0152760 | A1 | 8/2004 | Castillo et al. |
| 2005/0008664 | A1 | 1/2005 | Claxton et al. |
| 2005/0129781 | A1 | 6/2005 | Skiendzielewski et al. |

FOREIGN PATENT DOCUMENTS

| | | |
|---|---|---|
| CN | 1440747 | 9/2003 |
| CN | 1511518 | 7/2004 |
| DE | 10305768 | 8/2004 |
| EP | 705601 | 1/2000 |
| JP | 59-157008 | 9/1984 |
| KR | 2005001556 | 1/2005 |
| WO | 90/08759 | 8/1990 |
| WO | 97/27848 | 8/1997 |
| WO | 01/49281 | 7/2001 |
| WO | 03/089576 | 10/2003 |
| WO | 03/089577 | 10/2003 |
| WO | 2004/052294 | 6/2004 |

OTHER PUBLICATIONS

Okamoto et al. Digestive Diseases and Sciences. Oct. 2005. vol, 50, Supplement 1, pp. S34-S38.*
Papagergiou et al., "Study on the Antibiotic Fraction of *Alkanna Tinctoria Tausch*," Chimika Chronika, New Series, vol. 9, No. 1, 57-63 (1980).
International Search Report and Written Opinion issued for Application No. PCT/US07/66224, dated Aug. 25, 2008, 12 pages.
Manganiotis, Angelos N. MD, et al., "Urologic Complications of Crohn's Disease", Surgical Clinics of North America, vol. 81, No. 1, Feb. 2001, pp. 197-215.
Pardi, Darrell S. MD, et al., "Renal and Urologic Complications of Inflammatory Bowel Disease", The American Journal of Gastroenterology, vol. 93, No. 4, 1998, pp. 504-514.
Wong, Cathy, "Rhubarb Fact Sheet", About.com Alternative Medicine, http://altmedicine.about.com/od/completeazindex/a/rhubarb.htm?p-1, Updated: Mar. 30, 2006.

* cited by examiner

*Primary Examiner*—Sreeni Padmanabhan
*Assistant Examiner*—Samira Jean-Louis
(74) *Attorney, Agent, or Firm*—Howrey LLP; Viola T. Kung

(57) ABSTRACT

This invention relates compositions containing compounds of formula (I) below:

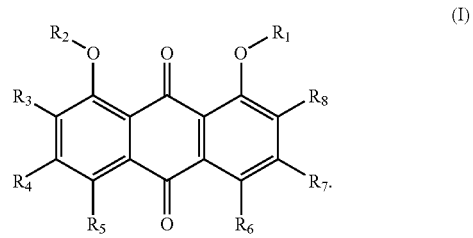

Each of $R_1$, $R_2$, $R_3$, $R_4$, $R_5$, $R_6$, $R_7$, and $R_8$ is defined in the specification.

21 Claims, No Drawings

ANTHRACENEDIONE COMPOUNDS

RELATED APPLICATIONS

This application claims priority to U.S. Provisional Application No. 60/790,340, filed on Apr. 7, 2006, the contents of which are incorporated herein by reference.

BACKGROUND

Constipation, a common and uncomfortable condition, affects about 20% of the population in the west. It is most often caused by a low-fiber diet, lack of physical activity, inadequate intake of water, or delay in going to the bathroom. Stress and travel also contribute to constipation. Other causes include bowel diseases (e.g., inflammatory bowel disease and irritable bowel syndrome), cystic fibrosis, pregnancy, mental health problems, or medication.

A balanced diet, regular exercise, and reduced stress can help prevent constipation. In addition, a number of laxatives are clinically proven to provide effective relief from constipation. However, these treatments have been unsatisfactory as evidenced by new therapies. Thus, there is a need for an alternative treatment for constipation.

SUMMARY

This invention relates to compositions and methods for treating constipation.

In one aspect, this invention relates to a pharmaceutical composition, either in a dry form or a solubilized from, containing a pharmaceutically acceptable enteric carrier and an anthracenedione compound of formula (I):

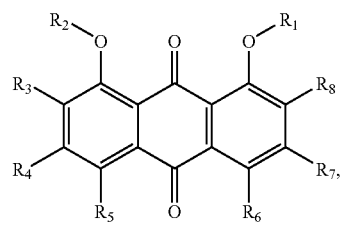

in which each of $R_1$ and $R_2$, independently, is H, $C_1$-$C_6$ alkyl, or C(O)$R_a$; each of $R_3$, $R_5$, $R_6$, and $R_8$, independently, is H, $C_1$-$C_6$ alkyl, or O$R_b$; and each of $R_4$ and $R_7$, independently, is H, O$R_c$, COO$R_c$, OC(O)O$R_d$, S$R_d$, NH$R_d$, or $C_1$-$C_6$ alkyl optionally substituted with $C_3$-$C_{20}$ cycloalkyl, $C_1$-$C_{20}$ heterocycloalkyl, aryl, heteroaryl, O$R_c$, COO$R_d$, OC(O)O$R_d$, S$R_d$, or NH$R_d$; in which each of $R_a$ and $R_c$ is $C_1$-$C_{10}$ alkyl; and each of $R_b$ and $R_d$, independently, is H or $C_1$-$C_{10}$ alkyl.

The compounds described above include their pharmaceutically acceptable salts and their metal complexes. The salts can be formed, e.g., between a negatively charged oxygen in a compound and a positively charged inorganic or organic ion. The metal complexes can be formed, e.g., the oxygen atoms on the compounds coordinate with one or more metallic ions.

Referring to formula (I), a subset of the anthracenedione compounds described above are those in which each of $R_4$ and $R_7$, independently, is H, $C_1$-$C_6$ alkyl (e.g., $CH_3$), or O$R_c$ (e.g., O$CH_3$). In these compounds, each of $R_1$, $R_2$, $R_3$, $R_5$, $R_6$, and $R_8$ can be H. Exemplary anthracenedione compounds include chrysophanol and physcion:

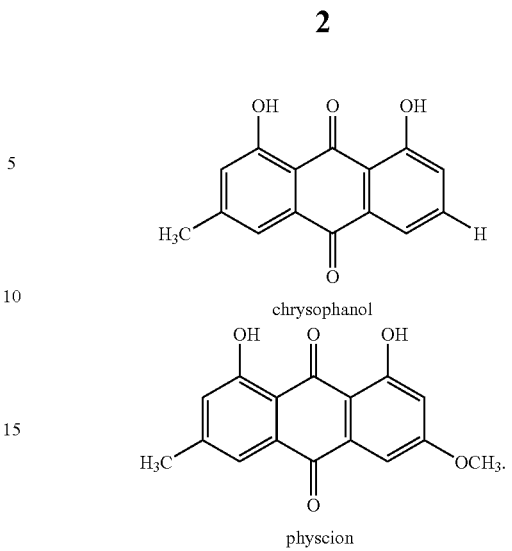

The term "alkyl" refers to a saturated or unsaturated, linear or branched hydrocarbon moiety, such as —$CH_3$, —$CH_2$—CH=$CH_2$, or branched —$C_3H_7$. The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom (e.g., N, O or S), such as 4-tetrahydropyranyl or 4-pyranyl. The term "aryl" refers to a hydrocarbon moiety having one or more aromatic rings. Examples of aryl moieties include phenyl, phenylene, naphthyl, naphthylene, pyrenyl, anthryl, and phenanthryl. The term "heteroaryl" refers to a moiety having one or more aromatic rings that contain at least one heteroatom (e.g., N, O or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl, and indolyl.

Alkyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_3$-$C_{20}$ cycloalkyl, $C_1$-$C_{20}$ heterocycloalkyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl can also be fused with each other.

The anthracenedione compounds described above can be used to treat constipation, i.e., improve intestinal motility while maintaining normal intestinal function. Increased intestinal motility shortens the duration for food to stay in the intestine. As a result, the intestine absorbs less food, which often includes carbohydrate, fat, cholesterol, low density lipoprotein, or triglyceride. Accordingly, the anthracenedione compounds allow a subject to decrease the body's intake of these nutrients and thereby (i) decrease cholesterol or triglycerides levels or (ii) reduce or maintain the body weight. Thus, this invention also relates to a method of using these compositions to improve intestinal motility and maintain normal intestinal function, to decrease cholesterol, low density lipoprotein, or triglycerides levels, and to reduce or maintain the body weight.

In yet another aspect, this invention relates to a method of treating inflammatory bowel disease or irritable bowel syndrome using the above-mentioned anthracenedione compounds.

Also within the scope of this invention are (1) use of the anthracenedione compounds described above in treating constipation, inflammatory bowel disease, or irritable bowel syndrome, improving intestinal motility and maintaining normal intestinal function, decreasing cholesterol, low density lipoprotein, or triglycerides levels, or reducing or maintaining the body weight; and (2) use of the anthracenedione compounds for the manufacture of a medicament or dietary supplement for the just-mentioned applications.

The details of one or more embodiments of the invention are set forth in the description below. Other features, objects, and advantages of the invention will be apparent from the description and the claims.

DETAILED DESCRIPTION

This invention is based, at least in part, on the unexpected discovery that two anthracenedione compounds, chrysophanol and physcion, found in Chinese herb *Rheum palmatum* Linne, are each effective in treating constipation. They do not have the side effects often seen in herb extracts prepared from the *Rheum palmatum* Linne, e.g., cramping, bloating, gas, and diarrhea. Further, each compound has a very low enteric absorption rate and therefore has minimal overall side effects to the body.

Accordingly, within the scope of this invention is a composition that contains an enteric carrier and one or more of the anthracenedione compounds described in the Summary section above. An enteric carrier is designed to minimize any fast release of a drug upon oral administration until the drug reaches the intestine. See, e.g., U.S. Pat. Nos. 5,188,836 and 6,306,434.

The composition can be a pharmaceutical composition that contains a pharmaceutically acceptable carrier or a dietary composition that contains a dietary suitable carrier. Preferably, an anthracenedione compound is added to the composition in pure form or substantially pure form. Anthracenedione compounds for use in this invention can be chemically synthesized or purified from herbs. For example, physcion and chrysophanol can be isolated from plants listed below in Tables A and B, respectively.

TABLE A

Physcion-containing Plants

| Family | Species |
|---|---|
| Lycopodiaceae | *Lycopodium japonicum* Thunb. |
| | *Lycopodium obscurum* L. |
| Urticaceae | *Boehmeria tricuspis* (Hance) Makino |
| Polygonaceae | *Polygonum ciliinerve* (Nakai) Ohwi |
| | *Polygonum cuspidatum* Sieb. et Zucc. |
| | *Polygonum multiflorum* Thunb. |
| | *Polygonum multiflorum* Thunb. |
| | *Pteroxygonum giraldii* Dammer et Diels |
| | *Rheum alexandrae* Batal. |
| | *Rheum hotaoense* C Y Cheng et T. C. Keo |
| | *Rheum likiangense* Sam. |
| | *Rheum nobile* Hook. f. et Thoms. |
| | *Rheum officinale* Baill. |
| | *Rheum palmatum* L. |

TABLE A-continued

Physcion-containing Plants

| Family | Species |
|---|---|
| | *Rheum palmatum* L. |
| | var. *tanguticum* Maxim. ex Regel |
| | *Rumex acetosa* L. |
| | *Rumex chalepensis* Mill. |
| | *Rumex dentatus* L. |
| | *Rumex gmelini* Turcz. |
| | *Rumex hastatus* D. Don |
| | *Rumex japonicus* Houtt. |
| | *Rumex nepalensis* Spreng. |
| | *Rumex obtusifolius* L. |
| | *Rumex patientia* L. |
| | *Rumex patientia* L. |
| | subsp. *tibeticus* (Reich. f.) Reich. f. |
| Berberidaceae | *Dysosma majorensis* (Gagnep.) Ying |
| | *Dysosma versipellis* (Hance) M. Cheng ex Ying |
| | *Dysosma pleiantha* (Hance) Woods. |
| | *Dysosma veitchii* (Hemsl. et Wils.) Fu ex Ying |
| Lardizabalaceae | *Sargentodoxa cuneata* (Oliv.) Rehd. et Wils. |
| Actinidiaceae | *Actinidia chinensis* Planch. |
| Leguminosae | *Abrus cantoniensis* Hance |
| | *Cassia angustifolia* Vahl. |
| | *Cassia acutifolia* Delile |
| | *Cassia nomame* (Sieb.) Kitag. |
| | *Cassia abtusifolia* L. |
| | *Cassia tora* L. |
| Rhamnaceae | *Rhamnus cathartica* L. |
| | *Rhamnus crenata* Sieb. et Zucc. |
| | *Rhamnus frangula* L. |
| | *Rhamnus napalensis* (Wall.) Laws. |
| | *Sageretia thea* (Osbeck) Johnst. |
| | *Ventilago leiocarpa* Benth. |
| Rubhceae | *Morinda officinalis* How. |
| | *Rubia cordifolia* L. |
| Asteraceae | *Saussurea laniceps* Hand.-Mazz. |
| | *Saussurea gnaphaloides* (Royle) Sch.-Bip. |
| | *Saussurea medusa* Maxim. |
| | *Saussurea tridactyla* Sch.-Bip. Ex Hook. f. |
| Pandanaceae | *Pandanus tectorius* Soland. |
| Orchidaceae | *Bletilla striata* (Thumb.) Reichb. f. |

TABLE B

Chrysophanol-containing Plants

| Family | Species |
|---|---|
| Taxaceae | *Amentotaxus argotaenia* (Hance) Pilger. |
| Polygonaceae | *Polygonum cuspidatum* Sieb. et Zucc. |
| | *Polygonum multiflorum* Thunb. |
| | *Polygonum perfoliatum* L. |
| | *Polygonum suffultum* Maxim. |
| | *Rheum alexandrae* Batal. |
| | *Rheum delavayi* Franch. |
| | *Rheum emodi* Wall. |
| | *Rheum franzenbachii* Munt. |
| | *Rheum hotaoense* C Y Cheng et T. C. Keo. |
| | *Rheum likiangense* Sam. |
| | *Rheum nobile* Hook. f. et Thoms. |
| | *Rheum officinale* Baill. |
| | *Rheum palmatum* L. |
| | *Rheum palmatum* L. |
| | var. *tanguticum* Maxim. ex Regel |
| | *Rumex acetosa* L. |
| | *Rumex acetosa* L. |
| | *Rumex chalepensis* Mill. |
| | *Rumex crispus* L. |
| | *Rumex dentatus* L. |
| | *Rumex gmelini* Turcz. |
| | *Rumex hastatus* D. Don |
| | *Rumex japonicus* Houtt. |
| | *Rumex nepalensis* Spreng. |
| | *Rumex maritimus* L. |

TABLE B-continued

Chrysophanol-containing Plants

| Family | Species |
|---|---|
| | *Rumex obtusifolius* L. |
| | *Rumex patientia* L. |
| | *Rumex patientia* L. |
| | subsp. *tibeticus* (Reich. f.) Reich. f. |
| Lardizabalaceae | *Sargentodoxa cuneata* (Oliv.) Rehd. et Wils. |
| Leguminosae | *Abrus cantoniensis* Hance. |
| | *Cassia angustifolia* Vahl. |
| | *Cassia acutifolia* Delile |
| | *Cassia mimosoides* L. |
| | *Cassia nomame* (Sieb.) Kitag. |
| | *Cassia abtusifolia* L. |
| | *Cassia tora* L. |
| | *Cassia occidentalis* L. |
| Simaroubaceae | *Brucea javanica* (L.) Merr. |
| Rhamnaceae | *Rhamnus cathartica* L. |
| | *Rhamnus crenata* Sieb. et Zucc. |
| | *Rhamnus davurica* Pall. |
| | *Rhamnus davurica* Pall. |
| | *Rhamnus frangula* L. |
| Umbelliferae | *Ligusticum chuanxiong* Hort. |
| Acanthaceae | *Baphicacanthus cusia* (Nees) Bremek. |
| Liliaceae | *Hemerocallis fulva* (L.) L. |
| | *Hemerocallis lilio-asphodelus* L. |

Examples of a composition of the present invention include, but are not limited to, foods, food additives, nutritional supplements, and pharmaceutical preparations. It may be in the form of tablets, suspensions, implants, solutions, emulsions, capsules, powders, syrups, liquid compositions, ointments, lotions, creams, pastes, gels, or the like.

A dietary composition of this invention, either in a dry form or a solubilized from, contains one or more of the anthrecenedione compounds and an edible carrier. Additional nutrients, such as minerals or amino acids, may be included. A dietary composition can also be a drink or food product. Examples of a drink product include, but are not limited to, tea-based beverages, juice, coffee, and milk. Examples of a food product include jelly, cookies, cereals, chocolates, snack bars, herbal extracts, dairy products (e.g., ice cream, and yogurt), soy bean product (e.g., tofu), and rice products.

A pharmaceutical composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A composition of the present invention includes a carrier. Depending on the kind of the composition, a carrier may be a suitable dietary carrier or a pharmaceutically acceptable carrier. Examples of a pharmaceutically acceptable carrier include, but are not limited to, biocompatible vehicles, adjuvants, additives, and diluents to achieve a composition usable as a dosage form.

A "pharmaceutically acceptable carrier" refers to a carrier that, after administration to or upon a subject, does not cause undesirable physiological effects. The carrier in a pharmaceutical composition must be "acceptable" also in the sense that it is compatible with the active ingredient and, preferably, capable of stabilizing it. One or more solubilizing agents can be utilized as pharmaceutical carriers for delivery of an active anthracenedione compound. Examples of other carriers include colloidal silicon oxide, magnesium stearate, cellulose, sodium lauryl sulfate, and D&C Yellow #10.

The above-described composition, in any of the forms described above, can be used for treating constipation. In fact, as shown in the examples below, the composition increased the production of feces and feces water content in a subject without causing side effects such as diarrhea. Also, it was effective in reducing or maintaining the body weight of the subject.

The term "treating" refers to administering an effective amount an anthrecenedione compound to a subject that has a disorder, e.g., constipation, inflammatory bowel disease, or irritable bowel syndrome, or has a symptom of such a disorder, or has a predisposition toward such a disorder, with the purpose to cure, heal, alleviate, relieve, alter, remedy, ameliorate, improve, or affect the disorder, the symptoms of the disorder, or the predisposition toward the disorder. The term "administration" covers oral delivery to a subject a composition of the invention in any suitable form, e.g., food product, beverage, tablet, capsule, suspension, and solution. An "effective amount" refers to a dose of the composition that is sufficient to provide a physical benefit (e.g., increasing feces production and reducing the body weight) or a therapeutic benefit (e.g., lowering cholesterol levels). Both in vivo and in vitro studies can be conducted to determine optimal administration routes and doses. Increasing feces production refers to an increase in the wet weight of feces produced by a subject by 15% or more one day after the subject receives an active composition as determined by the method described in Example 3 below or any analogous method.

A composition of the present invention may be used alone or in combination with other biologically active ingredients. It may be administered to a subject in a single dose or multiple doses over a period of time, generally by oral administration. Various administration patterns will be apparent to those skilled in the art. The dosage ranges for the administration of the composition are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be determined by one of skill in the art without undue experimentation. The dosage can be adjusted in the event of any counter indications, tolerance, or similar conditions. Those of skill in the art can readily evaluate such factors and, based on this information, determine the particular effective concentration of a composition of the present invention to be used for an intended purpose.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Aloe-emodin, rhein, emodin, chrysophanol, and physcion were isolated from a *Rheum palmatum* Linne extract STD-05. To prepare STD05, 3.2 kg *Rheum palmatum* was extracted with 12 L of ethyl acetate for 18 hours twice. The resulting solution was filtered through a 200 mesh filter. The filtrate was concentrated under vacuum, dissolved in 2 L of 95% ethanol, and precipitated with 6 L of water. The precipitant was then dissolved in 95% ethanol and precipitated again with water to generate "Fr-I" precipitant. The supernatant was fractionated in a Diaion HP-20 column and eluted with 30% ethanol, followed by 95% ethanol and ethyl acetate. Elutes fractionated from 95% ethanol (Fr-D) and from ethyl acetate (Fr-E) were combined with Fr-I as STD05. Twenty grams of STD05 was dissolved in ethyl acetate and mixed with a small amount of silica gel. Ethyl acetate was then removed under vacuum to give a mixture. The mixture was purified on a silica gel column eluting with 0% to 5% ethyl acetate in hexanes. Fractions thus obtained were analyzed by HPLC. Five compounds were detected by HPLC. Fractions of each compound were combined, respectively. The solvent of each combined solution was removed under vacuum to give five solid products. The solid products were recrystallized from acetone to give 220 mg of aloe-emodin, 290 mg of rhein, 1270 mg of emodin, 2220 mg of chrysophanol, and 790 mg of physcion. The results are summarized in Table 1 below:

TABLE 1

Compound Isolation

| Compounds | Eluent Hexanes:Ethyl Acetate | Weight (mg) | Yield (%) From the extract | From the herb |
|---|---|---|---|---|
| Aloe-emodin | 20:1 | 220 | 1.10 | 0.012 |
| Rhein | 20:1 | 290 | 1.45 | 0.016 |
| Emodin | 40:1 | 1270 | 6.35 | 0.071 |
| Chrysophanol | 180:1 | 2220 | 11.10 | 0.125 |
| Physcion | 160:1 | 790 | 3.95 | 0.044 |

Each of the isolated compounds was crystallized and examined under a microscope.

EXAMPLE 2

The laxative activities by *Rheum palmatum* Linne extracts were studied. A crude *Rheum palmatum* Linne extract and STD05 were obtained from SunTen Phytotech Co., Ltd. (Jhonghe City, Taiwan). Commercial available laxatives, Through® (Chung Mei Pharmaceutical Co., Ltd.; active ingredient: Sennosides 20 mg, as Sennosides A+B 12 mg, Lot. 009A 051) and Dulcolax® (Boehringer Ingelheim, Taiwan, Ltd.; active ingredient: Bisacodyl; Lot. 4804942) were obtained from a pharmacy.

Forty-two healthy male S.D. rats (8 weeks old; National Laboratory Animal Center, Taiwan) were divided into seven groups (six in each) and tested for the laxative activity by *Rheum palmatum* Linne extracts. The rats in one group were not fed with any extract or drug and used as negative controls. The rats in the second and third group were given Sennosides (3.55 mg/kg) and Bisacodyl (1.75 mg/kg), respectively, and used as positive controls. The Rats in the other four groups were given *Rheum palmatum* Linne crude extract (500 mg/kg), filtered crude extract STD03 (180 mg/kg), and STD05 (STD05-1: 12 mg/kg and STD05-2: 24 mg/kg), respectively. All substances were administered orally everyday for three weeks.

The experiments were carried out under conditions in which temperature, humidity, and lighting were all controlled. Each rat was fed standard rat food and water ad libitum in housing that provided a 12-hour light/dark cycle. The rats were divided into seven groups according to the body weights.

The first part of the experiment studied the effect of the above-mentioned extracts on feces production. During the three-week period, any rat that appeared dying was euthanized, dissected, and studied to check for any illness or injures. Any complications or illness were analyzed by H&E stains to determine the cause of death and to allow for dosage reconsiderations for future experiments.

During this period, the body weights of the rats were weighed each day and recorded. Feces of each rat were studied three times during the period for any unusual observations. Specifically, the amounts of feces were weighed on Days 11, 15, 18, and 21. During observation, each rat was placed in a metabolic cage. Feces were collected every twenty-four hours. The number of collected feces pellets was counted, and the pellets' shapes and colors were evaluated. After weighing the moist feces, they were dried in an oven at 100° C. for twenty-four hours. The water content from the feces was calculated according to the following formula:

$$\text{Water content percentage} = [(\text{wet weight} - \text{dry weight})/\text{wet weight}] \times 100\%. \quad (I)$$

The results are summarized in Table 2 below:

TABLE 2

Effects of *Rheum palmatum* Linne extracts on feces production

| | | Control | *Rheum palmatum* | Bisacodyl | Sennosides | STD03 | STD05-1 | STD05-2 |
|---|---|---|---|---|---|---|---|---|
| Day 11 | Wet Weight (g) | 21.66 | 39.46 | 33.84 | 29.21 | 27.60 | 22.79 | 22.59 |
| | Pellet count | 87 | 178 | 116 | 121 | 126 | 105 | 116 |
| | Water content (%) | 48.82 | 56.92 | 64.45 | 52.70 | 53.35 | 50.19 | 42.07 |
| Day 15 | Wet Weight (g) | 16.86 | 28.50 | 41.64 | 30.95 | 36.86 | 27.34 | 29.09 |
| | Pellet count | 84 | 139 | 110 | 119 | 153 | 130 | 124 |
| | Water content (%) | 42.89 | 49.53 | 68.34 | 60.40 | 57.19 | 47.57 | 48.83 |
| Day 18 | Wet Weight (g) | 22.14 | 24.98 | 30.14 | 23.90 | 25.01 | 24.51 | 29.48 |
| | Pellet count | 90 | 126 | 81 | 106 | 124 | 114 | 123 |
| | Water content (%) | 43.83 | 48.36 | 66.65 | 47.30 | 49.40 | 47.63 | 50.19 |
| Day 21 | Wet Weight (g) | 22.79 | 36.52 | 40.13 | 27.80 | 24.18 | 24.51 | 27.17 |
| | Pellet count | 91 | 105.6 | 108 | 123 | 115 | 97 | 108 |
| | Water content (%) | 47.85 | 63.89 | 68.02 | 44.73 | 47.56 | 51.10 | 43.54 |

After the above-discussed feces tests, intestinal motility tests were conducted. Before the experiment, the rats were fasted for at least sixteen hours. The rats were then given the aforementioned drugs or extracts. After 3 hours, each rat was given 3 ml/kg of 0.5% methylcellulose solution–0.5% Evans blue dye. Each rat was sacrificed 30 minutes later and its abdominal cavity was cut open. The entire small intestine was extracted and carefully straightened. The entire stretch between the pylorous and cecum was measured as the small intestine length. The distance traveled by Evans blue dye along the intestines was also measured. During dissection, any unusual observations were recorded and photographed. The intestinal motility function was calculated in the following formula:

$$\text{Intestine motility} = (\text{Evans blue dye length/small intestine length}) \times 100\%. \quad (II)$$

The results are summarized in Table 3 below.

TABLE 3

Effects of *Rheum palmatum* Linne extracts on intestine motility.

| STD03 | | | STD05-1 | | | STD05-2 | | |
|---|---|---|---|---|---|---|---|---|
| Small intestine length (cm) | Dye length (cm) | Intestinal motility (%) | Small intestine length (cm) | Dye length (cm) | Intestinal motility (%) | Small intestine length (cm) | Dye length (cm) | Intestinal motility (%) |
| 105 | 83.5 | 79.5 | 101 | 77.5 | 76.7 | 117 | 83.5 | 71.4 |
| 118.5 | 75 | 63.3 | 102.5 | 72.5 | 70.7 | 114 | 89 | 78.1 |
| 111 | 80.5 | 72.5 | 113.5 | 105 | 92.5 | 112 | 99.5 | 88.8 |
| 110 | 79 | 71.8 | 107 | 70 | 65.4 | 107 | 89 | 83.2 |
| 120 | 87 | 72.5 | 110 | 86 | 78.2 | 101 | 86 | 85.1 |
|  |  |  | 108 | 77.5 | 71.8 | 118.5 | 81 | 68.4 |
|  | Mean | 71.9 |  | Mean | 75.9 |  | Mean | 79.2 |
|  | SD | 5.8 |  | SD | 9.3 |  | SD | 8.1 |

Intestine motility data were expressed as mean±SD. Data were analyzed using the one-way ANOVA method. For comparison within the groups, a Post hoc Comparison was applied. In both feces production and intestine motility analyses, $p<0.05$ indicates significant differences. For the feces production tests, the data for each group and each time point represent the total wet weight or pellet count of the six rats in the group.

EXAMPLE 3

The aforementioned STD05 and compounds were studied for the laxative activity. Healthy male S.D. rats (BioLASCO Taiwan Co. Ltd.) were divided into three groups (i.e., Groups 1-3) in this study.

In Group I, 6 rats, as negative control, were given no treatment; 6 rats, as positive control, were given 3.35 mg/kg/day Sennosides (Through®, Chung Mei Pharmaceutical Co., Ltd,; Active ingredient: Sennosides 20 mg, as sennoside A+B 12 mg, Lot. 012F 006); 6 rats were treated STD05 (8 mg/kg/day); 6 rats were treated with an extract fraction containing aloe-emodin, rhein, and emodin ("ARE", 8 mg/kg/day); 6 rats were treated with Aloe-emodin (4 mg/kg/day); and 6 rats were treated with Rhein (4 mg/kg/day).

In Group II, 6 rats, as negative control, were given no treatment; 6 rats, as positive control, were given 3.35 mg/kg/day Sennosides; 6 rats were treated STD05 (24 mg/kg/day); 6 rats were treated with an extract fraction containing ARE (24 mg/kg/day); 6 rats were treated with Chrysophanol (4 mg/kg/day); and 6 rats were treated with Emodin (4 mg/kg/day).

In Group III, 6 rats, as negative control, were given no treatment; 6 rats were treated with Physcoin (4 mg/kg/day); and 6 rats were treated with a mixture of chrysophanol and physcion (8 mg/kg/day, "CP").

The experiments were carried out under controlled temperature, humidity, and lighting. Each rat was fed standard rat food and water ad libitum in housing that provided a 12-hour light/dark cycle. For statistical comparison, all of the rats were divided into six sets according to the body weights.

The first part of the experiment studied the effect of the test substances on feces production. During the 10-day period, the body weights of the rats were weighed each day and recorded. The rat's feces was also studied three times in the manner described above during the 10-day period for any unusual observations. During the 10-day period, any rat that appeared dying was euthanized, dissected, and examined for any illness or injury. Any complications or illness were analyzed by H&E stains to determine the cause of death and to allow for dosage reconsiderations for future experiments. Summarized in Table 4 below are the effects of the compounds, mixtures, or extracts on the rat body weights.

TABLE 4

Effects of compounds and *Rheum palmatum* Linne extracts on body weight

| | | Group I Control | | | Group II Control | | | Group III Control | | |
|---|---|---|---|---|---|---|---|---|---|---|
| | | Start Day 1 | End Day 10 | Difference | Start Day 1 | End Day 10 | Difference | Start Day 1 | End Day 10 | Difference |
| | | 280 | 335 | 55 | 355 | 400 | 45 | 415 | 450 | 35 |
| | | 285 | 345 | 60 | 365 | 405 | 40 | 430 | 460 | 30 |
| | | 290 | 355 | 65 | 365 | 410 | 45 | 435 | 470 | 35 |
| | | 275 | 330 | 55 | 345 | 385 | 40 | 405 | 440 | 35 |
| | | 285 | 345 | 60 | 360 | 410 | 50 | 425 | 460 | 35 |
| | | 295 | 355 | 60 | 380 | 435 | 55 | 450 | 475 | 25 |
| Mean | | 285 | 344 | 59 | 362 | 408 | 46 | 427 | 459 | 33 |
| SD | | 7 | 10 | 4 | 12 | 16 | 6 | 16 | 13 | 4 |
| | | Sennosides | | | Sennosides | | | | | |
| | | Start Day 1 | End Day 10 | Difference | Start Day 1 | End Day 10 | Difference | Start Day 1 | End Day 10 | Difference |
| | | 280 | 325 | 45 | 340 | 370 | 30 | | | |
| | | 285 | 330 | 45 | 350 | 395 | 45 | | | |

TABLE 4-continued

Effects of compounds and *Rheum palmatum* Linne extracts on body weight

|      |     |     |    |     |     |    |
|------|-----|-----|----|-----|-----|----|
|      | 290 | 350 | 60 | 365 | 405 | 40 |
|      | 275 | 310 | 35 | 325 | 360 | 35 |
|      | 285 | 350 | 65 | 370 | 410 | 40 |
|      | 295 | 365 | 70 | 390 | 445 | 55 |
| Mean | 285 | 338 | 53 | 357 | 398 | 41 |
| SD   | 8   | 20  | 14 | 23  | 30  | 9  |

| | STD05 (8 mg/kg) | | | STD05 (24 mg/kg) | | | | | |
|---|---|---|---|---|---|---|---|---|---|
| | Start Day 1 | End Day 10 | Difference | Start Day 1 | End Day 10 | Difference | Start Day 1 | End Day 10 | Difference |
|      | 275 | 330 | 55 | 345 | 380 | 35 | | | |
|      | 285 | 345 | 60 | 355 | 385 | 30 | | | |
|      | 290 | 350 | 55 | 360 | 395 | 35 | | | |
|      | 275 | 335 | 60 |     |     |    | | | |
|      | 285 | 345 | 60 |     |     |    | | | |
|      | 295 | 355 | 65 | 375 | 395 | 20 | | | |
| Mean | 285 | 343 | 59 | 359 | 389 | 30 | | | |
| SD   | 7   | 15  | 4  | 13  | 8   | 7  | | | |

| | ARE (8 mg/kg) | | | ARE (24 mg/kg) | | | | | |
|---|---|---|---|---|---|---|---|---|---|
| | Start Day 1 | End Day 10 | Difference | Start Day 1 | End Day 10 | Difference | Start Day 1 | End Day 10 | Difference |
|      | 270 | 325 | 55 | 335 | 370 | 35 | | | |
|      | 285 | 345 | 60 | 360 | 405 | 45 | | | |
|      | 295 | 350 | 55 | 370 | 405 | 35 | | | |
|      | 280 | 325 | 45 | 335 | 370 | 35 | | | |
|      | 285 | 345 | 60 | 355 | 395 | 40 | | | |
|      | 290 | 365 | 75 | 375 | 435 | 60 | | | |
| Mean | 284 | 343 | 58 | 355 | 397 | 42 | | | |
| SD   | 9   | 15  | 10 | 17  | 25  | 10 | | | |

| | Aloe-emodin (4 mg/kg) | | | Chrysophanol (4 mg/kg) | | | Physcion (4 mg/kg) | | |
|---|---|---|---|---|---|---|---|---|---|
| | Start Day 1 | End Day 10 | Difference | Start Day 1 | End Day 10 | Difference | Start Day 1 | End Day 10 | Difference |
|      | 270 | 315 | 45 | 330 | 370 | 40 | 385 | 410 | 25 |
|      | 285 | 335 | 50 | 350 | 370 | 20 | 400 | 430 | 30 |
|      | 295 | 345 | 50 | 355 | 385 | 30 | 405 | 450 | 45 |
|      | 275 | 315 | 40 | 325 | 350 | 25 | 365 | 385 | 20 |
|      | 285 | 325 | 40 | 340 | 370 | 30 | 385 | 415 | 30 |
|      | 290 | 345 | 55 | 360 | 410 | 50 | 430 | 460 | 30 |
| Mean | 283 | 330 | 58 | 343 | 376 | 33 | 395 | 425 | 30 |
| SD   | 9   | 14  | 10 | 14  | 20  | 11 | 22  | 28  | 8  |

| | Rhein (4 mg/kg) | | | Emodin (4 mg/kg) | | | CP (8 mg/kg) | | |
|---|---|---|---|---|---|---|---|---|---|
| | Start Day 1 | End Day 10 | Difference | Start Day 1 | End Day 10 | Difference | Start Day 1 | End Day 10 | Difference |
|      | 275 | 330 | 55 | 340 | 370 | 30 | 390 | 415 | 25 |
|      | 280 | 330 | 50 | 345 | 380 | 35 | 395 | 420 | 25 |
|      | 285 | 340 | 55 | 360 | 405 | 45 | 430 | 455 | 25 |
|      | 275 | 310 | 35 | 330 | 340 | 10 | 360 | 385 | 25 |
|      | 280 | 335 | 55 | 350 | 385 | 35 | 405 | 435 | 30 |
|      | 285 | 340 | 55 | 360 | 395 | 35 | 405 | 440 | 35 |
| Mean | 280 | 331 | 51 | 348 | 379 | 32 | 398 | 425 | 28 |
| SD   | 4   | 11  | 8  | 12  | 23  | 12 | 23  | 24  | 4  |

As shown in Table 4, STD05 and the compounds are effective in maintaining the body weight. It was unexpected that pure form of each compound was also effective.

During the period, feces produced by the rats were studied days 1, 5, and 10 in the same manner described above. It was found that STD05 promoted feces production. In the 10-day period, the rats administered with STD05 produced more feces (wet weight) that the rats in the control group by about 32%. In addition, the pellet counts for the rats administered with STD05 were greater than those for the control rats by about 20%. Furthermore, STD05 increased the water content in feces by about 18%. The same experiments were conducted on rats administered with physcion, aloe-emodin, chrysophanol, rhein, emodin, CP, and ARE. The results are summarized in Table 5 below:

parison was applied with p<0.05 indicating significant differences. It was found that the rat received STD05 (containing Physcion and Chrysophanol) and Sennosides had greater intestinal motility (69.3% and 67.9%) than the control rats (61.1%).

EXAMPLE 4

STD05 was tested in Guinea pig ileum electrical stimulation increase tissue assay at test concentrations ranging from 10 nm to 10 µM by MDS Pharma Services. The assay was conducted according to the method described in Moritoki, et al., "Effects of methylxanthines and imidazole on the contraction of guinea pig ileum induced by transmural simulation" Eur. J. Pharmacol. 35, 185-198.

TABLE 5

Effects of compounds and extracts on feces production

| Group I | | Control | Sennosides (3.35 mg/kg) | STD05 (8 mg/kg) | ARE (8 mg/kg) | Aloe-emodin (4 mg/kg) | Rhein (4 mg/kg) |
|---|---|---|---|---|---|---|---|
| Day 1 | Wet Weight (g) | 13.42 | 18.72 | 14.06 | 9.43 | 17.00 | 17.57 |
| | Pellet count | 85 | 101 | 79 | 63 | 98 | 102 |
| | Water content (%) | 32.59 | 45.69 | 39.73 | 32.54 | 42.48 | 42.58 |
| Day 5 | Wet Weight (g) | 18.48 | 26.16 | 27.76 | 18.53 | 20.21 | 16.88 |
| | Pellet count | 90 | 119 | 119 | 82 | 104 | 89 |
| | Water content (%) | 39.83 | 48.68 | 48.44 | 47.35 | 41.98 | 44.55 |
| Day 10 | Wet Weight (g) | 24.15 | 36.38 | 33.83 | 19.87 | 28.86 | 23.52 |
| | Pellet count | 93 | 146 | 125 | 89 | 125 | 119 |
| | Water content (%) | 49.11 | 57.4 | 54.55 | 48.36 | 50.48 | 46.53 |

| Group II | | Control | Sennosides (3.35 mg/kg) | STD05 (24 mg/kg) | ARE (24 mg/kg) | Chrysophanol (24 mg/kg) | Emodin (4 mg/kg) |
|---|---|---|---|---|---|---|---|
| Day 1 | Wet Weight (g) | 24.15 | 36.19 | 37.27 | 17.62 | 28.86 | 16.86 |
| | Pellet count | 99 | 134 | 125 | 67 | 128 | 90 |
| | Water content (%) | 51.11 | 61.09 | 60.65 | 50.21 | 50.82 | 42.38 |
| Day 5 | Wet Weight (g) | 22.85 | 36.42 | 27.28 | 18.60 | 26.48 | 25.51 |
| | Pellet count | 94 | 118 | 109 | 79 | 119 | 112 |
| | Water content (%) | 49.70 | 61.53 | 55.47 | 50.73 | 51.22 | 51.00 |
| Day 10 | Wet Weight (g) | 25.29 | 36.21 | 31.07 | 25.66 | 28.83 | 26.21 |
| | Pellet count | 84 | 132 | 101 | 107 | 127 | 106 |
| | Water content (%) | 48.64 | 53.99 | 62.19 | 53.35 | 56.52 | 53.64 |

| Group III | | Control | Physcion (4 mg/kg) | CP (8 mg/kg) |
|---|---|---|---|---|
| Day 1 | Wet Weight (g) | 18.32 | 35.38 | 28.74 |
| | Pellet count | 65 | 134 | 115 |
| | Water content (%) | 49.51 | 55.73 | 52.82 |
| Day 5 | Wet Weight (g) | 22.41 | 35.17 | 31.26 |
| | Pellet count | 78 | 128 | 112 |
| | Water content (%) | 50.93 | 53.80 | 56.36 |
| Day 10 | Wet Weight (g) | 22.37 | 29.43 | 26.37 |
| | Pellet count | 91 | 121 | 106 |
| | Water content (%) | 47.09 | 47.66 | 50.93 |

As shown in Table 5, during the 10-day period, except ARE, all compounds promoted feces production in the order of physcion>CP>aloe-emodin>chrysophanol>rhein>emodin (from the most potent to the least potent). For example, physcion, CP, aloe-emodin, chrysophanol, rhein, and emodin increased the feces amount (wet weight) by 93%, 57%, 27%, 19%, 31%, and −30%, respectively, at Day 1; by 57%, 39%, 9%, 16%, −9%, and 12%, respectively, at Day 5; and by 32%, 18%, 20%, 14%, −1%, and 4%, respectively, at Day 10. The averages are 61%, 38%, 19%, 16%, 7%, and −5%, respectively.

After finishing the feces tests, intestinal motility tests were conducted in the same manner described above. During dissection, any unusual observations were recorded and photographed. For comparison within the groups, a Post hoc Com- The results show that STD05 increased neurogenic twitch by 36% at the concentrations of 0.03 and 0.3 µM and caused reduction in the post-treatment basal twitch response of −24% at the concentration of 10 µM.

EXAMPLE 5

STD05 was evaluated for possible hypocholesterolemic activity in hamsters fed with a high cholesterol diet. STD05 at 30 and 100 mg/kg was administered orally once a day for 14 consecutive days. Blood was drawn from overnight fasted hamsters on day 1 (pre-treatment), day 8 (7 days post dosing), and day 15 (14 days post dosing) to measure serum total cholesterol, high density lipoprotein, low density lipoprotein and triglyceride levels. Post-treatment values on day 8 and day 15 were expressed in percentage of respective pretreatment values (day) in order to assess lipid-lowering effect of the tested composition. Decrease of 20% or more in total cholesterol or low density lipoprotein or increase of 20% or more in high density lipoprotein as well as decrease of 40% or more in triglyceride relative to the vehicle group were considered significant. Also one-way ANOVA followed by Dunnet's test was applied for statistical comparison between the vehicle and treated groups.

The results show that STD05 at the concentration of 100 mg/kg had significant low-density lipoprotein lowering effect. The effect became evident after the two week treatment.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating an inflammatory bowel disease in a subject, comprising administering to the subject in need thereof an effective amount of a purified compound of formula (I):

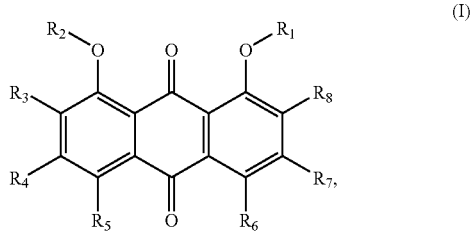

wherein
each of $R_1$, $R_2$, $R_3$, $R_4$, $R_5$, $R_6$, and $R_8$, independently, is H, or $C_1$-$C_6$ alkyl; and
$R_7$ is $OR_c$;
in which $R_c$ is $C_1$-$C_{10}$ alkyl.

2. The method of claim 1, wherein said compound is administered in a composition comprising a pharmaceutically acceptable carrier.

3. The method of claim 1, wherein the inflammatory bowel disease is Crohn's disease or ulcerative colitis.

4. The method of 2, wherein the pharmaceutically acceptable carrier is an enteric carrier.

5. The method of claim 1, wherein $R_7$ is $OCH_3$.

6. The method of claim 1, wherein each of $R_1$, $R_2$, $R_3$, $R_5$, $R_6$, and $R_8$ is H.

7. The method of claim 2, wherein the composition is in a dry form.

8. The method of claim 1, wherein $R_4$ is $C_1$-$C_6$ alkyl.

9. The method of claim 8, wherein $R_4$ is $CH_3$.

10. The method of claim 9, wherein each of $R_1$, $R_2$, $R_3$, $R_5$, $R_6$, and $R_8$ is H.

11. The method of claim 1, wherein the compound is physcion.

12. A method for treating an inflammatory bowel disease comprising feeding a subject in need thereof an effective amount of a purified compound of formula (I), in a form of a dietary composition:

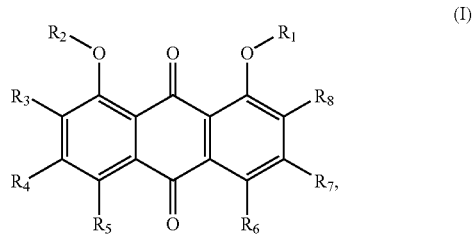

wherein
each of $R_1$, $R_2$, $R_3$, $R_4$, $R_5$, $R_6$, and $R_8$, independently, is H, or $C_1$-$C_6$ alkyl; and
$R_7$ is $OR_c$,
in which $R_c$ is $C_1$-$C_{10}$ alkyl.

13. The method of claim 12, wherein $R_4$ is $C_1$-$C_6$ alkyl.

14. The method of claim 13, wherein $R_4$ is $CH_3$.

15. The method of claim 14, wherein each of $R_1$, $R_2$, $R_3$, $R_5$, $R_6$, and $R_8$ is H.

16. The method of claim 15, wherein the composition is in a dry form.

17. The method of claim 12, wherein the dietary composition is a tea, soft drink, juice, milk, coffee, jelly, ice cream, yogurt, cookie, cereal, chocolate, snack bar, candy, chewing gum, syrup, or food capsule.

18. The method of claim 12, wherein $R_7$ is $OCH_3$.

19. The method of claim 18, wherein each of $R_1$, $R_2$, $R_3$, $R_5$, $R_6$, and $R_8$ is H.

20. The method of claim 12, wherein said dietary composition comprises an edible carrier.

21. The method of claim 12, wherein compound is physcion.

* * * * *